United States Patent

Dickens et al.

[11] Patent Number: 6,120,499
[45] Date of Patent: Sep. 19, 2000

[54] INTRAVASCULAR RF OCCLUSION CATHETER

[75] Inventors: Duane Dickens, Fremont; Gene Samson, Milpitas; Ruey Sung, Hillsborough, all of Calif.

[73] Assignee: Cardima, Inc., Fremont, Calif.

[21] Appl. No.: 08/582,600

[22] Filed: Jan. 3, 1996

Related U.S. Application Data

[63] Continuation of application No. 08/207,918, Mar. 8, 1994, abandoned.

[51] Int. Cl.⁷ ..................................................... A61B 17/36
[52] U.S. Cl. .............................. 606/41; 600/374; 606/31; 607/101; 607/122
[58] Field of Search ................. 606/27–31, 41, 606/42, 45–50; 607/100–102, 122; 128/642; 600/374

[56] References Cited

U.S. PATENT DOCUMENTS

| | | | |
|---|---|---|---|
| 4,660,571 | 4/1987 | Hess et al. ................................. | 606/49 |
| 4,735,201 | 4/1988 | O'Reilly ..................................... | 606/28 |
| 4,785,815 | 11/1988 | Cohen . | |
| 4,840,186 | 6/1989 | Lekholm et al. ........................ | 607/116 |
| 4,896,671 | 1/1990 | Cunningham et al. . | |
| 4,920,980 | 5/1990 | Jackowski . | |
| 4,966,597 | 10/1990 | Cosman . | |
| 4,985,028 | 1/1991 | Isner et al. . | |
| 4,998,933 | 3/1991 | Eggers et al. ............................. | 606/41 |
| 5,056,517 | 10/1991 | Fenici . | |
| 5,057,105 | 10/1991 | Malone et al. ............................ | 606/31 |
| 5,098,431 | 3/1992 | Rydell . | |
| 5,122,136 | 6/1992 | Guglielmi et al. ........................ | 606/41 |
| 5,122,137 | 6/1992 | Lennox ..................................... | 606/40 |
| 5,151,100 | 9/1992 | Abele et al. .............................. | 606/28 |
| 5,222,501 | 6/1993 | Ideker et al. . | |
| 5,230,349 | 7/1993 | Langberg . | |
| 5,254,088 | 10/1993 | Lundquist et al. . | |
| 5,281,212 | 1/1994 | Savage et al. . | |
| 5,281,213 | 1/1994 | Milder et al. . | |
| 5,281,217 | 1/1994 | Edwards et al. . | |
| 5,281,218 | 1/1994 | Imran . | |
| 5,293,868 | 3/1994 | Nardella . | |
| 5,295,484 | 3/1994 | Marcus et al. . | |
| 5,309,910 | 5/1994 | Edwards et al. . | |
| 5,315,996 | 5/1994 | Lundquist . | |
| 5,318,525 | 6/1994 | West et al. . | |
| 5,342,357 | 8/1994 | Nardella .................................... | 606/38 |
| 5,370,644 | 12/1994 | Langberg ................................ | 607/156 |
| 5,437,664 | 8/1995 | Cohen et al. ............................ | 606/38 |

FOREIGN PATENT DOCUMENTS

| | | |
|---|---|---|
| 0 499 491 A3 | 8/1992 | European Pat. Off. . |
| 0 600 676 A2 | 11/1993 | European Pat. Off. . |
| 93-20747 | 1/1993 | WIPO . |
| 93/20877 | 10/1993 | WIPO . |

*Primary Examiner*—Michael Peffley
*Attorney, Agent, or Firm*—Heller Ehrman White & McAuliffe

[57] ABSTRACT

The invention is directed to an intravascular device for occluding a patient's blood vessel by coagulating blood in a desired location within the blood vessel to form occluding thrombus therein by means of RF electrical energy which preferably has a frequency of about 0.3 to about 1.5 megahertz. The intravascular device is particularly useful in terminating arrhythmia in a patient's heart by occluding a coronary artery to terminate the flow of oxygenated blood to a region of the patient's heart where aberrant signals causing the arrhythmia either originate or through which they are conducted. The device may also be used to occlude other blood vessels such as in the treatment of intracranial berry aneurysms.

53 Claims, 3 Drawing Sheets

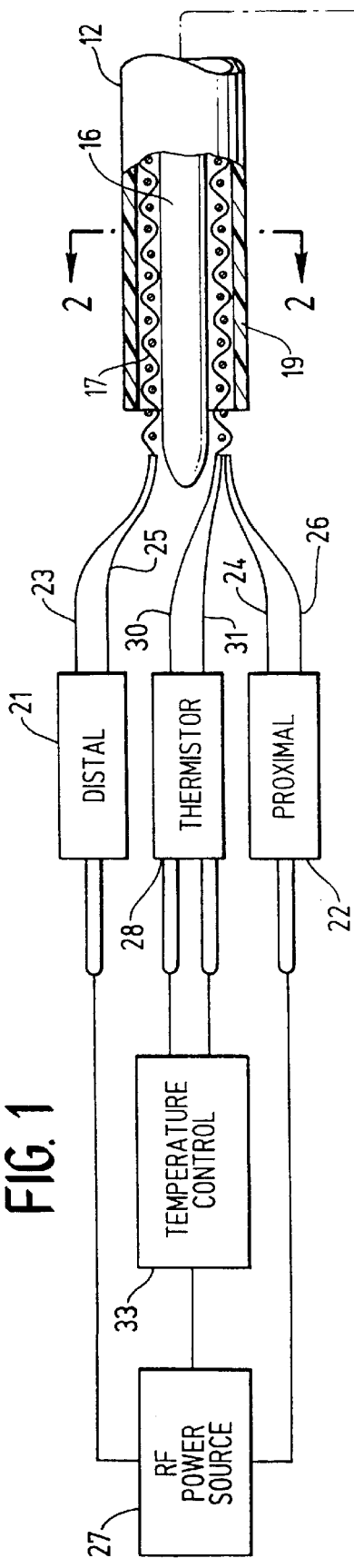
FIG. 1
FIG. 2
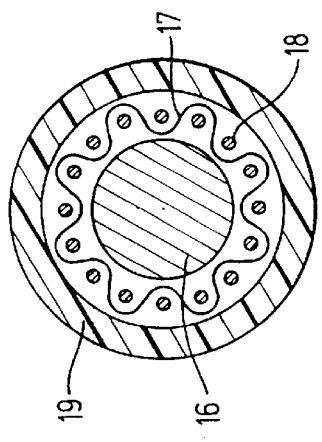

INTRAVASCULAR RF OCCLUSION CATHETER

This is a continuation of application Ser. No. 08/207,918, which was filed on Mar. 8, 1994 now abandoned.

BACKGROUND OF THE INVENTION

This application is directed to an elongated intravascular device for the occlusion of an arterial passageway by forming thrombus therein for therapeutic purposes and particularly to the treatment of arrhythmia.

A frequently used method for treating a patient's heart exhibiting arrhythmia includes the use of antiarrhythmic drugs such as sodium and calcium channel blockers or drugs which reduce the Beta-adrenergic activity. Other methods include the surgically sectioning the origin of the signals causing the arrhythmia or a conducting pathway for such signals. Lately, however, a frequently used method to terminate the arrhythmia is to destroy the heart tissue at the site from which the signals causing the arrhythmia originate or at a pathway through which such signals pass. The latter methods of destroying tissue at such a site include applying laser or radio frequency (RF) energy to the patient's endocardium at or close to the site from within the patient's left or right ventricle in order to destroy heart tissue involved with the arrhythmia and thereby terminate the irregular heart beat. For example, the average arrhythmogenic site consists of about 1.4 $cm^2$ of endocardial tissue, whereas a re-entrant site might be much larger. Presently used RF ablation techniques produce lesions about 0.5 $cm^2$ in diameter, so a number of lesions usually must be generated in order to completely ablate the area of interest. If the site is not accurately mapped or if there is difficulty in accurately placing the distal tip of the ablation device, much good tissue which is neither the cause of nor involved with the arrhythmia surrounding the site will be unnecessarily destroyed.

The prior ablation methods typically used elongated intravascular devices which are advanced through the patient's vasculature until the distal portion of the intravascular device is disposed within one of the patient's heart chambers with the ablating means such as an RF emitting electrode or the distal end of an laser delivering optical fiber in contact with the desired region of the patient's endocardium. While this procedure is now widely practiced, it is difficult to precisely position the distal ablation portion of the intravascular device at the desired location where the tissue causing or involved with the arrhythmia is to be destroyed.

What has been needed and heretofore unavailable is a method and system which quickly destroys tissue causing or involved with the but which does not destroy an excessive amount of uninvolved tissue adjacent to the site. The present invention satisfies these and other needs.

SUMMARY OF THE INVENTION

This invention is directed to an elongated intravascular device which forms thrombus within an arterial passageway with RF energy to occlude the passageway for therapeutic purposes, destroying heart tissue which causes arrhythmia or which is involved with the conductance of signals which cause arrhythmia.

In accordance with one aspect of the present invention, heart tissue which causes or is involved with a patient's heart exhibiting arrhythmia is destroyed by coagulating or electrocoagulating blood or both within a coronary artery feeding such heart tissue so as to form thrombus therein and thereby prevent the flow of sufficient oxygenated blood to the tissue. The ischemic conditions at the site of the tissue leads to an infarct which in turn terminates the arrhythmia. However, the elevated temperatures of the surfaces of the elongated device causing the coagulation should not be high enough to cause significant tissue damage and generally should range from about 70° to about 120° C., preferably about 85° to about 105° C. In a presently preferred method, coagulation is caused by delivery of RF energy to the blockage site at frequencies of about 0.3 to about 1.5 megahertz, preferably about 0.7 to about 1.2 megahertz. Typical power levels for effective thrombus formation for arterial occlusion may range from about 2 to about 10 watts, usually about 3 to about 7 watts.

A presently preferred intravascular device of the invention comprises an elongated shaft with a proximal section and a distal section with at least one emitting electrode on the distal end and preferably at least one sensing electrode spaced proximally from emitting electrode. Electrical conductors are secured by their distal ends to the emitting and sensing electrodes and by their proximal ends to a source of RF energy and a signal display unit respectively. The distal section of the shaft is configured so as to be advanceable through the patient's coronary anatomy and particularly through coronary arteries having native diameters less than 0.04 inch (1 mm), and frequently less than 0.025 inch (0.64 mm). The outer diameter of the distal portion may range from about 0.001 to about 0.025 inch (0.77–2 mm).

The elongated shaft of the device may be formed of a plurality of insulated electrical conductors braided or wound into an elongated tubular member, although not all of the strands which make up the tubular member need be electrical conductors. For example, one or more of the strands may be formed of a high strength non-metallic material such as nylon. The diameter of the conductors are preferably quite small, e.g. 0.001 to about 0.005 inch (0.025–0.127 mm), typically about 0.003 inch (0.08 mm) to facilitate the braiding or winding of the wires and to maintain tubular member flexibility. However, due to the small diameter of the conductors, two or more conductors may be required to carry the needed electrical power to an emitting electrode. The emitting and sensing electrodes are suitably secured to the conductors by soldering but other methods such as a mechanical connection may be used.

An elongated core member is disposed within an inner lumen extending the length of the tubular member. The distal extremity of the core member extending through the distal section is shielded by an insulating plastic tubular member which may be formed of a material such a polyamide. In some embodiments the core member may be utilized as a conductor for transmitting RF energy to an emitting electrode on the distal end of the shaft. A temperature sensing element such as a thermistor may be provided in the distal section of the shaft which is electrically connected to conductors which may also be incorporated into the braided or wound structure forming the tubular member. This facilitates controlling the temperature of the distal tip of the device to avoid excessive pain or tissue damages. The catheter may also be provided with an expandable member, e.g. an inflatable balloon, close to but proximal to the emitting electrode(s) to center the distal extremity of the catheter within the arterial passageway to avoid thermal damage to the artery wall and to provide a more effective formation of thrombus in the arterial passageway.

The emitting electrode on the distal end of the elongated intravascular device in one presently preferred embodiment has a concave distal surface which concentrates the RF energy in a location within the arterial passageway distal to the distal end of the catheter. The edges of the outer tubular member are formed about the outer circular edge of the concave distal face of the distal emitting electrode to avoid thrombus formation on these edges and ensure that most if not all of the thrombus is formed distal to the catheter.

While the present invention is described herein primarily in terms of treating a patient's heart exhibiting arrhythmia, those skilled in the art will recognize that the device may be utilized in a variety of bodily locations for various therapeutic reasons, e.g. the embolization of an intracranial berry aneurysm.

The elongated intravascular device of the invention can be readily advanced into a patient's coronary, intracranial and other arteries, and, upon delivery of RF energy to the emitting electrode or electrodes on the distal extremity of the device, coagulation rapidly occurs within the arterial passageway, preferably distal to the distal end of the catheter, so as to occlude the artery and create the ischemic conditions needed for the therapeutic purposes, e.g. to terminate an arrhythmia or to prevent the rupture of an aneurysm. One or more of the emitting electrodes may be conveniently used as a sensing electrode along with one or more other sensing electrodes to verify the location of the ectopic foci within the patient's heart prior to the delivery of RF energy to occlude the artery and after the procedure to ensure that the arrhythmia has been terminated. These and other advantages of the invention will become apparent from the following detailed description of the invention when taken in conjunction with the accompanying drawings.

BRIEF DESCRIPTION OF THE DRAWINGS

FIG. 1 is a elevational view, partially in longitudinal section, of an elongated intravascular device embodying features of the invention.

FIG. 2 is a transverse cross-sectional view of the intravascular device shown in FIG. 1 taken along the lines 2—2.

DETAILED DESCRIPTION OF THE INVENTION

Figure 3:
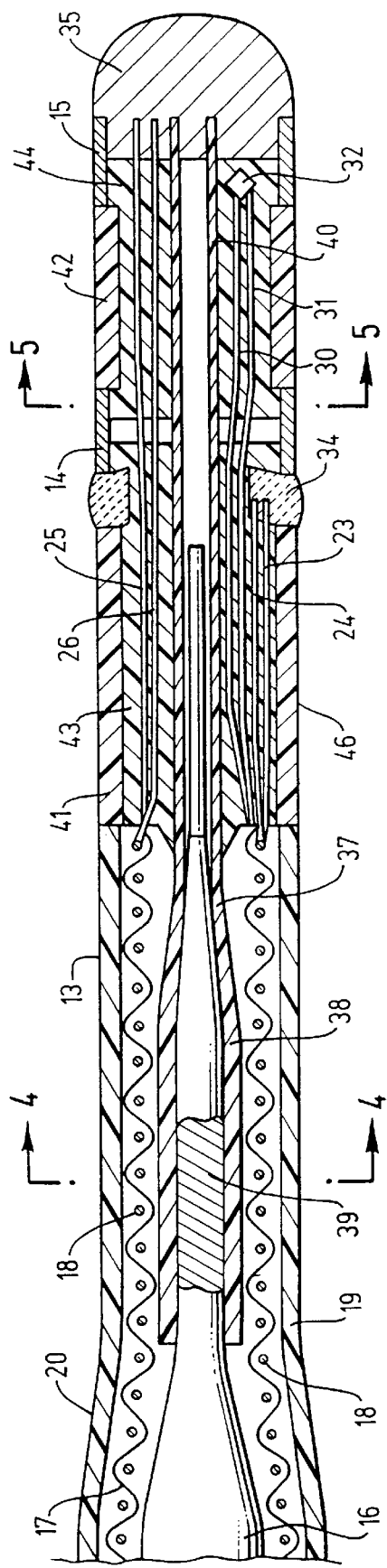
FIG. 3 is an enlarged longitudinal cross-sectional view of the distal section of the intravascular device shown in FIG. 1 taken along the lines 3—3.

A presently preferred embodiment of the invention is schematicly illustrated in FIGS. 1–5. As shown, the elongated intravascular device 10 has an elongated shaft 11 with proximal section 12 and a distal section 13, the distal section having a proximal emitting electrode 14 and distal emitting electrode 15. The shaft 11 of the intravascular device 10 generally comprises a core member 16, a braided or wound tubular member 17, which is formed of a plurality of electrical conductors 18, and an outer plastic jacket or covering 19 disposed about the braided or wound tubular member 17. The proximal section 12 is much longer and has a larger diameter than the distal section 13 and a tapered transition 20 is provided between the two sections. While only one transition is shown a plurality of transitions may be provided to more gradually reduce the outer diameter of the device from the proximal section 12 to the distal section 13.

The proximal end of the shaft 11 has single pin connectors 21 and 22 which are connected to the proximal electrode 14 and the distal electrode 15, respectively, through conductors 23 and 24 and 25 and 26, respectively as shown. Multiple conductors may be employed to supply RF electrical power to each of the emitting electrodes 14 and 15 in order to deliver a level of electrical power adequate for rapid electrocoagulation yet allow for the use of smaller diameter conductors which are easier to braid or wind and which form a more flexible tubular member 17. The single pin connectors 21 and 22 are in turn electrically connected to an RF electrical power source 27. A two pin connector 28 is electrically connected through conductors 30 and 31 to a temperature sensing element 32 (shown in FIG. 3) in the distal section 13. The two pin connector 28 is electrically connected to a temperature control system 33 which controls the RF output of the electrical power source 27. Simple on-off controls or comprehensive feed back controls of the power source 27 based on impedance, power and the like may be used, as is apparent to those skilled in the art.

Figure 5:
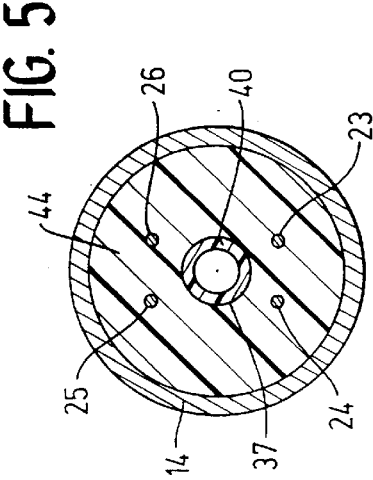
FIG. 5 is a transverse cross-sectional view of the distal section of the intravascular device shown in FIG. 3 taken along the lines 5—5.
Figure 4:
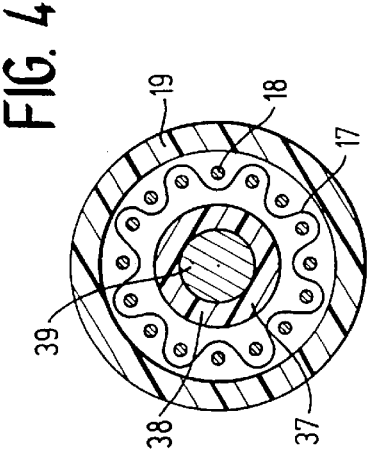
FIG. 4 is a transverse cross-sectional view of the distal section of the intravascular device shown in FIG. 3 taken along the lines 4—4.

As shown in more detail in FIGS. 3–5, the proximal electrode 14 is electrically connected by solder 34 to electrical conductors 23 and 24 and distal electrode 15 is electrically connected to electrical conductors 25 and 26 by solder ball tip 35. The solder ball tip 35 is provided with a rounded semi-spherical shape to minimize traumatic engagement with arterial walls as the intravascular device is advanced through the patient's arterial system, particularly the coronary arteries.

The distal section 13 of the intravascular device 10 has a tubular insulation shield 37 with an enlarged proximal portion 38 secured to the small diameter distal portion 39 of the core member 16 and a smaller diameter distal portion 40 which extends to and is secured to the solder ball tip 35. The shield 37 is preferably formed of polyamide tubing because such material is strong and insulating and it has sufficient high temperature properties that it can be soldered without significant damage. The portion of the distal section 13 on which the electrodes 14 and 15 are mounted is formed in part by a pair of plastic tubes 41 and 42 which are preferably formed of low density polyethylene with insulating filler 43 and 44, e.g epoxy resin disposed within the interior of the tubes. Temperature sensor 32, preferably a thermistor with a resistance of about 1000 to about 2000 ohms, typically about 1500 ohms, is disposed close to the solder ball tip 35 to ensure accurate temperature measurements.

The dimensions of the intravascular device are typical of intravascular devices which are configured to be advanced within a patient's coronary arteries. The overall length is about 80 to about 150 cm, depending upon whether the device is advanced through the femoral artery or the brachycephalic artery. The outer diameter of the proximal section 12 of the shaft 11 is about 0.016 to about 0.035 inch (0.41–0.89 mm), typically about 0.022 inch (0.56 mm) and the outer diameter of the distal section thereof is about 0.01 to about 0.022 inch (0.25–0.56 mm), typically about 0.012 to about 0.018 inch (0.41–0.46 mm). The core member 16 has a typical diameter of about 0.013 inch (0.33 mm) in the proximal portion, and a rectangular distal portion of about 0.006 inch (0.15 mm) by 0.002 inch (0.05 mm) in the distal portion thereof. The distal section 12 is about 5 to about 40 cm in length and is generally configured to be readily advancable through a patient's tortuous coronary arteries.

The distal tip 46 on which electrodes 14 and 15 are mounted is rather short and is usually less than one cm in length. Typically, the electrodes are about 0.5 mm in length and the plastic tubes 41 and 42 are about 0.25 to about 1.5 mm in length. The electrical conductors forming the tubular member 17 are about 0.0015 to about 0.005 inch (0.04–0.13 mm) in outer diameter, typically about 0.003 inch (0.08 mm), and are usually provided with an insulating coating or jacket formed of suitable insulating material such polyamide. In the presently preferred embodiment depicted in the drawings, the braided tubular member 17 is formed by sixteen strands, six electrical conductors and ten filler strands of nylon about the same size as the electrical conductors.

To the extent not previously discussed the materials and methods of construction may be typical for catheters and guidewires used in coronary arteries.

The intravascular device of the present invention is preferably introduced into the patient's arterial system percutaneously or by means of a cut-down into the femoral artery and advanced through the aorta into the ostium of the desired coronary artery. A guiding catheter is usually employed, as in conventional angioplasty procedures, to guide the intravascular device of the invention to the desired coronary artery. The distal end of the guiding catheter is seated in the ostium of the desired coronary artery. The distal section 13 of the device is advanced out the distal end of the guiding catheter into the patient's coronary artery to a distal location which has been previously determined to deliver blood to a very small area or region of the patient's heart from has the tissue which causes or in involved with the arrhythmia. RF electrical power is directed through conductors 23–26 to the electrodes 14 and 15 on the distal section 13 to heat up and thereby coagulate and to electrocoagulate blood about and distal to the distal tip 46, thereby forming thrombus which occludes the arterial passageway and create ischemic conditions which leads to an infarct which terminates the arrhythmia. The temperature at the distal tip 46 is determined by the thermistor 32. To effectively coagulate blood the temperature should be above about 80° C. but generally the temperature should not exceed about 120° C. to avoid excessive tissue damage to the surrounding area and to minimize the pain to the patient who may be lightly sedated for the procedure. In most instances there is no need to exceed a temperature higher than about 100° C. The coagulation of blood within the artery results from two factors, the first being the elevated temperatures and the second being electrocoagulation, both of which are caused by the RF energy. The length of time needed to completely occlude the artery will vary depending upon the inner diameter of the artery and the electrical power delivered to the emitting electrodes on the distal tip of the device. Care must be exercised to avoid introducing an excessive amount of electrical power which can injure the arterial wall.

Figure 6:
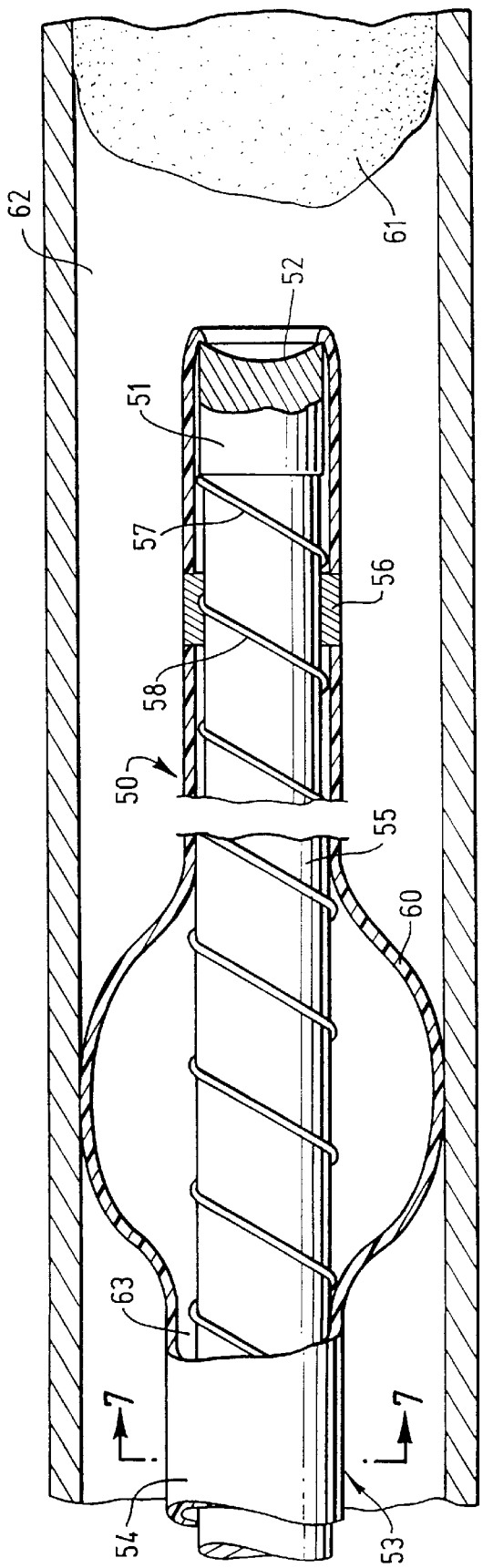
FIG. 6 is an elevational view, partially in section, of an alternative embodiment of the invention which has an emitting electrode on the distal end which can concentrate the RF energy distal to the catheter.
Figure 8:
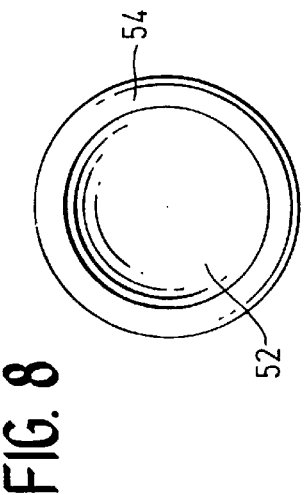
FIG. 8 is a front view of the distal end of the catheter.
Figure 7:
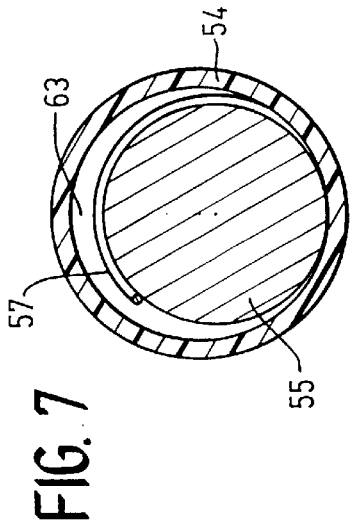
FIG. 7 is a transverse cross-sectional view of the embodiment shown in FIG. 6 taken along the lines 7—7.

FIGS. 6–8 schematically depict the distal extremity 50 of an alternative embodiment of the invention wherein an emitting electrode 51 having a concave shaped distal surface 52 is provided on the distal end of the catheter which concentrates or focuses the RF energy at a location distal to the distal extremity. The catheter shaft 53 includes an outer tubular member 54, an inner core member 55 which extends to and is suitable secured by solder or other means to the proximal end of the emitting electrode 51. As best shown in FIG. 6 the distal end of the outer tubular member 54 is shaped about the outer circular edge of the distal face 52 of the emitting electrode 51 to avoid thrombus formation along the edges and to ensure that most if not all of the thrombus is formed distal to the emitting electrode. A sensing electrode 56 is disposed on the exterior of the distal extremity 50 at a location proximal to the distal emitting electrode 51 on the distal end of the catheter. The sensing electrode 56 and the emitting electrode 51 may be used in a bipolar mode to detect electrical activity within the patient's heart so as to locate the tissue causing or involved with a patient's arrhythmia. Elongated conductors 57 and 58 are secured by their distal ends to the emitting electrode 51 and the sensing electrode 56 respectively and extend between the outer tubular member 54 and the core member 55. The conductors 57 and 58 may be wound about the core member 55 as shown in FIGS. 6 and 7. The depth of the concavity of the distal face of the emitting electrode 51 should not be greater than about one-half the diameter of the distal face, preferably not greater than about one quarter of the diameter of the distal face. An expandable balloon 60 is formed in the outer tubular member 54 which facilitates centering the distal extremity 50 of the catheter to ensure effective formation of thrombus 61 within the arterial passageway 62. Inflation lumen 63 defined between the outer tubular member 54 and the core member 55 directs inflation fluid to the interior of the balloon 60.

The location of the site of the patient's heart to be ablated with RF energy can be determined in a variety of ways. One method which has been found to be particularly suitable is that described in copending applications Ser. No. 08/010, 818, filed Jan. 29, 1993, application Ser. No. 08/043,449, filed Apr. 5, 1993, and application Ser. No. 08/057,294, filed May 5, 1993, and the applications filed on Jan. 27, 1994, of Laszlo Littmann and Duane Dickens entitled METHOD AND SYSTEM FOR USING MULTIPLE INTRAVASCULAR SENSING DEVICES TO DETECT ELECTRICAL ACTIVITY, of Laszlo Littmann, Gene Samson and Gabriel Vegh entitled INTRAVASCULAR SENSING DEVICE, and of Ruey Sung and Gene Samson entitled INTRAVASCULAR METHOD AND SYSTEM FOR TREATING ARRHYTHMIA, which are incorporated herein in their entirety by reference. In the methods described in these references, intravascular devices having a plurality of sensing electrodes are advanced through a patient's coronary arteries and cardiac veins to detect electrical activity of interest which facilitate locating the tissue causing arrhythmia. The emitting electrodes on the RF device are also used to verify the location of the ectopic foci prior to delivery of RF energy to the electrodes and to ensure that after the ablation there is no electrical activity which might cause or ultimately lead to the recurrence of arrhythmia.

While the present invention has been described herein in terms of certain presently preferred embodiments, those skilled in the art will recognize that various modifications and improvements can be made to the invention. For example, the core member is described herein as a solid elongated member, but it is readily apparent that the core member can be a small diameter hypotube. Other modification and improvements can be without departing from the scope of the invention.

What is claimed is:

1. An intravascular device for occluding a patient's artery comprising:
   a) an elongated shaft having a proximal and distal ends and a distal shaft portion which is configured to be advanced through a patient's artery having an outer diameter not greater than 0.025 inch;

b) a first electrode on the distal end of the elongated shaft which has a concave distal face for emission of high frequency electrical energy;

c) a second electrode on the distal extremity of the elongated shaft spaced proximal to the distal end of the shaft;

d) a plurality of insulated electrical conductors, each conductor having a distal and electrically connected to one of said electrodes and having a proximal end electrically connected to an electrical connector; and e) a source of high frequency electrical power electrically connected to at least one insulated electrical conductor by means of the electrical connector.

2. The intravascular device of claim 1 wherein the source of high frequency electrical power is a RF electrical power source.

3. The intravascular device of claim 2 wherein the RF electrical power source has an output with a frequency of about 0.3 to about 1.5 megahertz.

4. The intravascular device of claim 2 wherein the RF electrical power source has an output with a frequency of about 0.7 to about 1.2 megahertz.

5. The intravascular device of claim 1 wherein the catheter distal shaft portion has a diameter of at least about 0.01 inch.

6. The intravascular device of claim 1 wherein the distal shaft portion has an outer diameter of about 0.012 to about 0.018 inch.

7. The intravascular device of claim 1 wherein at least part of the elongated shaft has a thermoplastic fluoropolymer jacket on the exterior thereof.

8. An intravascular device for occluding a patient's artery comprising:

a) an elongated shaft having a proximal portion with a first outer diameter, a distal portion which is much shorter than the proximal portion and which is configured to be advanced through a patient's artery by having a second outer diameter smaller than the first outer diameter of the proximal portion; and including an inner lumen extending within the proximal and distal portions of the elongated shaft, an elongated core member disposed within the inner lumen of the elongated shaft, a plurality of insulated electrical conductors having proximal and distal ends, and an outer tubular member which is disposed about and extends along the elongated core member, defining at least in part the inner lumen;

b) at least one emitting electrode on the distal portion of the elongated shaft which is electrically connected to the distal end of an electrical conductor; and c) an electrical connector electrically connected to the proximal of the electrical conductor electrically connected to the emitting electrode and configured to electrically connect at least the electrical conductor to a source of RF electrical energy.

9. The intravascular device of claim 8 wherein a plurality of emitting electrodes are longitudinally spaced along the distal portion and are electrically isolated from each other.

10. The intravascular device of claim 8 including a RF electrical power source with the electrical connectors connected thereto.

11. The intravascular device of claim 10 wherein the RF electrical power source has an output with a frequency of about 0.3 to about 1.5 megahertz.

12. The intravascular device of claim 10 wherein the RF electrical power source has an output with a frequency of about 0.7 to about 1.2 megahertz.

13. The intravascular device of claim 8 wherein the outer tubular member is formed of a plurality of braided individually insulated electrical conductors.

14. The intravascular device of claim 8 wherein the distal shaft portion has an outer diameter of about 0.01 to about 0.025 inch.

15. The intravascular device of claim 8 wherein the distal shaft portion has an outer diameter of about 0.012 to about 0.018 inch.

16. The intravascular device of claim 8 wherein the core member is formed of a material selected from the group consisting of stainless steel and a nickel-titanium alloy having pseudoelastic properties at body temperature.

17. The intravascular device of claim 8 wherein a thermoplastic fluoropolymer jacket is provided on the exterior of the outer tubular member.

18. The intravascular device of claim 8 wherein a temperature sensing element is provided in the distal portion of the device.

19. The intravascular device of claim 18 wherein the temperature sensing element is electrically connected to a pair of conductors which form at least in part the tubular member.

20. The intravascular device of claim 8 including an expandable member on the distal portion of the shaft to position the distal portion within a passageway of the patient's artery.

21. The intravascular device of claim 20 wherein the expandable member is an inflatable balloon.

22. The intravascular device of claim 21 wherein the balloon is formed of elastic material.

23. The intravascular device of claim 8 wherein the emitting electrode is provided on the distal end of the shaft.

24. The intravascular device of claim 23 wherein the emitting electrode has a concave distal face.

25. The intravascular device of claim 24 wherein the concavity of the distal face in not greater than one-half the diameter of the distal face.

26. The intravascular device of claim 25 wherein the concavity is not greater than one-fourth the diameter of the distal face.

27. The intravascular device of claim 8 including at least one sensing electrode on the distal portion of the shaft for detecting electrical activity within the patient's artery.

28. The intravascular device of claim 8 wherein the core member is fixed within the inner lumen of the intravascular device.

29. The intravascular device of claim 28 wherein a temperature sensing element is provided in the distal shaft portion.

30. The intravascular device of claim 28 wherein an expandable member is provided on the distal shaft portion thereof to position the distal shaft portion within an arterial passageway.

31. The intravascular device of claim 30 wherein the expandable member is an inflatable balloon.

32. The intravascular device of claim 31 wherein the balloon is formed of elastic material.

33. The intravascular device of claim 1 wherein the concavity of the distal face of the first electrode is not greater than one-fourth the diameter of the distal face.

34. The intravascular device of claim 8 including at least one sensing electrode on the distal shaft portion for detecting electrical activity within a patient's blood vessel.

35. A method of treating a patient's heart experiencing arrhythmia wherein an arterial vessel leading to a portion of the patient's heart which causes or is involved with the arrhythmia is occluded, comprising:

a) providing an elongated intravascular device having at least one emitting electrode on a distal extremity thereof;

b) advancing the elongated intravascular device through the patient's vascular system to the arterial vessel which is to be occluded; and c) emitting RF electrical energy from at least one electrode on the distal extremity of the elongated intravascular device within the arterial vessel to coagulate blood to form thrombus therein which occludes the arterial vessel.

36. The method of claim 35 wherein the frequency of the RF electrical energy emitted into the arterial vessel at a frequency of about 0.3 to about 1.5 megahertz.

37. The method of claim 35 wherein the frequency of the RF electrical energy emitted into the arterial vessel at a frequency of about 0.7 to about 1.2 megahertz.

38. The method of claim 35 wherein the distal portion of the elongated device having at least one emitting electrode is advanced within the coronary artery to an arterial region having a native inner diameter of less than about 0.04 inch.

39. The method of claim 35 including controlling the temperature of the distal extremity of the elongated intravascular device between about 80° and about 120° C.

40. The method of claim 35 including detecting electrical activity by means of electrodes on the distal portion from within a coronary artery to ensure the proper location of the elongated device therein.

41. The method of claim 35 wherein the RF energy is concentrated within the arterial vessel to be occluded distal to an emitting electrode on the distal end of the intravascular device.

42. The method of claim 41 wherein the RF energy is concentrated distal to the electrode by means of a concave emitting surface on the distal end of the emitting electrode.

43. The method of claim 35 wherein the elongated intravascular device has at least one pair of sensing electrodes on the distal portion and electrical activity of the patient's heart is detected within the coronary artery by the sensing electrodes to determine the location of tissue which causes or is involved with arrhythmic conditions within the patient's heart.

44. A method of occluding a patient's arterial vessel which directs blood to heart tissue causing or involved with arrhythmia in order to terminate such arrhythmia, comprising:

a) providing an elongated intravascular device having at least one emitting electrode on a distal extremity thereof;

b) advancing the elongated intravascular device through the patient's vascular system until the at least one emitting electrode is at a location within the arterial vessel which is to be occluded; and c) emitting RF electrical energy from the at least one emitting electrode within the arterial vessel to coagulate blood to form thrombus therein which occludes the arterial vessel.

45. The method of claim 44 wherein the frequency of the RF electrical energy emitted into the arterial vessel is at a frequency of about 0.3 to about 1.5 megahertz.

46. The method of claim 44 wherein the frequency of the RF electrical energy emitted into the arterial vessel is at a frequency of about 0.7 to about 1.2 megahertz.

47. The method of claim 44 wherein the distal portion of the elongated device having at least one emitting electrode is advanced within the arterial vessel to a region therein having a native inner diameter of less than about 0.04 inch where the emitted RF energy forms thrombus to occlude the arterial vessel.

48. The method of claim 44 including controlling the temperature of the distal extremity of the elongated intravascular device between about 80° and about 120° C. when emitting RF energy.

49. The method of claim 44 including detecting electrical activity by means of electrodes on the distal portion from within the coronary artery to ensure the proper location of the elongated intravascular device therein.

50. The method of claim 44 wherein the RF energy is concentrated within the arterial vessel to be occluded distal to an emitting electrode on the distal end of the intravascular device.

51. The method of claim 44 wherein the RF energy is concentrated distal to the electrode by means of a concave emitting surface on the distal end of the emitting electrode.

52. An intravascular device for therapeutic or diagnostic procedures, comprising:

a) an elongated shaft having a proximal portion with a first outer diameter, a distal portion which is much shorter than the proximal portion and which has an outer diameter less than about 0.025 inch; and including
an inner lumen extending within the proximal and distal portions of the elongated shaft,
an elongated core member disposed within the inner lumen of the elongated shaft and extending within the distal portion of the elongated shaft,
at least one insulated electrical conductor having proximal and distal ends, and
an outer tubular member which is disposed about and extends along the elongated core member, defining at least in part the inner lumen;

b) at least one emission electrodes on the distal portion of the elongated shaft which is electrically connected to the distal end of an electrical conductor; and c) an electrical connector electrically connected to the proximal end of the intravascular device which is configured to electrically connect at least one electrical conductor to a source of RF electrical energy.

53. The intravascular catheter of claim 52 wherein the distal portion has an outer diameter less than 0.022 inch.

* * * * *